(12) United States Patent
Turner

(10) Patent No.: US 7,625,014 B2
(45) Date of Patent: Dec. 1, 2009

(54) DUAL FLUID CONNECTOR

(75) Inventor: Denis P. Turner, Vista, CA (US)

(73) Assignee: Alcon, Inc., Hunenberg (CH)

( * ) Notice: Subject to any disclaimer, the term of this patent is extended or adjusted under 35 U.S.C. 154(b) by 72 days.

(21) Appl. No.: 11/829,228

(22) Filed: Jul. 27, 2007

(65) Prior Publication Data

US 2008/0073906 A1     Mar. 27, 2008

Related U.S. Application Data

(60) Provisional application No. 60/847,180, filed on Sep. 26, 2006.

(51) Int. Cl.
*F16L 39/00* (2006.01)
*A61M 39/10* (2006.01)

(52) U.S. Cl. .............. 285/123.3; 285/123.12; 285/124.1; 285/124.3; 604/533

(58) Field of Classification Search ........... 285/123.1, 285/123.3, 123.12, 123.15, 124.1, 124.2, 285/124.3, 124.4, 247, 363, 124.5; 604/533, 604/534, 535
See application file for complete search history.

(56) References Cited

U.S. PATENT DOCUMENTS

| | | | |
|---|---|---|---|
| 515,119 A * | 2/1894 | Edwards | 285/363 |
| 1,389,768 A * | 9/1921 | McFarland | 285/123.3 |
| 1,481,255 A * | 1/1924 | Cumfer | 165/154 |
| 2,860,311 A * | 11/1958 | Balian | 333/248 |
| 3,109,671 A * | 11/1963 | Braun | 285/123.3 |
| 3,317,221 A * | 5/1967 | Brown | 285/39 |
| 3,469,863 A * | 9/1969 | Riester et al. | 285/124.4 |
| 3,948,315 A * | 4/1976 | Powell | 165/70 |
| 4,108,476 A * | 8/1978 | Krupp | 285/47 |
| 4,328,862 A * | 5/1982 | Gossalter | 165/158 |
| 4,732,414 A * | 3/1988 | Inaba | 285/123.15 |
| 5,088,774 A * | 2/1992 | Spiegelman | 285/123.1 |
| 5,184,850 A * | 2/1993 | Wermelinger | 285/21.2 |
| 5,431,641 A * | 7/1995 | Grozinger et al. | 604/533 |
| 5,628,532 A * | 5/1997 | Ashcraft | 285/123.15 |
| 5,655,794 A * | 8/1997 | Sell | 285/25 |
| 6,533,328 B2 * | 3/2003 | Takamatsu | 285/123.15 |
| 6,649,829 B2 | 11/2003 | Garber et al. | |
| 6,866,299 B2 * | 3/2005 | Coates | 285/123.15 |
| 6,897,374 B2 | 5/2005 | Garber et al. | |
| 7,052,047 B1 * | 5/2006 | Box et al. | 285/123.15 |
| 2004/0051308 A1 * | 3/2004 | Coates | 285/124.1 |
| 2007/0241560 A1 * | 10/2007 | Malone | 285/319 |
| 2008/0294144 A1 * | 11/2008 | Leo et al. | 604/508 |

FOREIGN PATENT DOCUMENTS

JP         02150593 A    *    6/1990

* cited by examiner

*Primary Examiner*—James M Hewitt
(74) *Attorney, Agent, or Firm*—W. David Lee

(57) ABSTRACT

A connector includes a rear body portion and a front body portion. The front side of the rear body portion, and the front body portion disposed therearound, are for fluidly coupling to first and second sources of pressurized fluids in a co-axial manner. The rear side of the rear body portion is for fluidly coupling to first and second destinations of the pressurized fluids in an adjacent manner.

12 Claims, 3 Drawing Sheets

DUAL FLUID CONNECTOR

This application claims the priority of U.S. Provisional Application Ser. No. 60/847,180 filed Sep. 26, 2006.

FIELD

The present invention pertains to connectors used in lines for conducting fluid; more particularly the present invention pertains to a dual fluid connector.

BACKGROUND

In many different types of equipment, particularly medical equipment, multiple fluids are often used during medical procedures to treat patients. One example of such medical equipment is a vitrectomy system used for operations on the eye or eyes of a patient. In a fluid/gas exchange performed during a vitrectomy surgery, there is often a need for a source of pressurized retinal tamponading gases (i.e. $C_3F_8$ and $SF_6$) as well as a need for a source of pressurized air.

Prior art connectors used to handle multiple fluids have presented several problems. Such problems include difficulty coupling the large number of tubes that conduct the pressurized fluids between their respective sources and destinations. This large number of tubes also necessitates a connector having a relatively large size. Accordingly, a need remains in the art for a small, simple connector that enables better management and connection of tubing used for such fluids.

SUMMARY

The present invention is a fluid connector that enables better management and connection of tubing used for medical or surgical fluids. The fluid connector has a rear body portion and a front body portion. The rear body portion has a rear side and a front side. The rear side has a center port and an off-center port, and the front side has a center projection with a center opening, a ring-shaped flange disposed around the center projection, and a ring-shaped channel defined by the center projection and the ring-shaped flange. The rear body portion also has a central passage extending through the rear body portion. The central passage originates at the center port and terminates at the center opening. The rear body portion also has an off-center passage extending through the rear body portion. The off-center passage originates at the off-center port and terminates at the ring-shaped channel. The front body portion is constructed and arranged for interfitment over the ring-shaped flange of the rear body portion and is for coupling with a manifold of a surgical console. The front body portion shrouds the center projection and further defines the ring-shaped channel.

BRIEF DESCRIPTION OF THE DRAWING FIGURES

A better understanding of the dual fluid connector of the present invention may be had by reference to the following drawing figures when read in conjunction with the following Description of the Embodiments.

DESCRIPTION OF THE EMBODIMENTS

The disclosed connector 10 is described herein according to its use with a vitrectomy console. However, those of ordinary skill in the art will understand its applicability to other ophthalmic surgical consoles as well as a variety of different types of other medical equipment, such as equipment used by dentists or veterinarians, or still other equipment requiring the use of multiple fluids in a procedure enabled by the medical equipment.

The preferred embodiment of the connector 10 described herein is used in connection with a system for performing a fluid/gas exchange during vitrectomy surgery. A preferred system is described in more detail in U.S. application Ser. No. 11/855,198, filed Sep. 14, 2007, and entitled "Surgical Console", which is commonly owned with the present invention and incorporated herein by reference. The disclosed connector 10 is fabricated from ABS plastic, and further includes two O-rings 44, 50 and an RFID tag 99. The RFID tag 99 is captured inside of a sonic welded two part assembly. In use, the design of the disclosed connector 10 delivers pressurized gas, either $C_3F_8$ or $SF_6$, through one internal passage and pressurized air through another internal passage.

Figure 1:
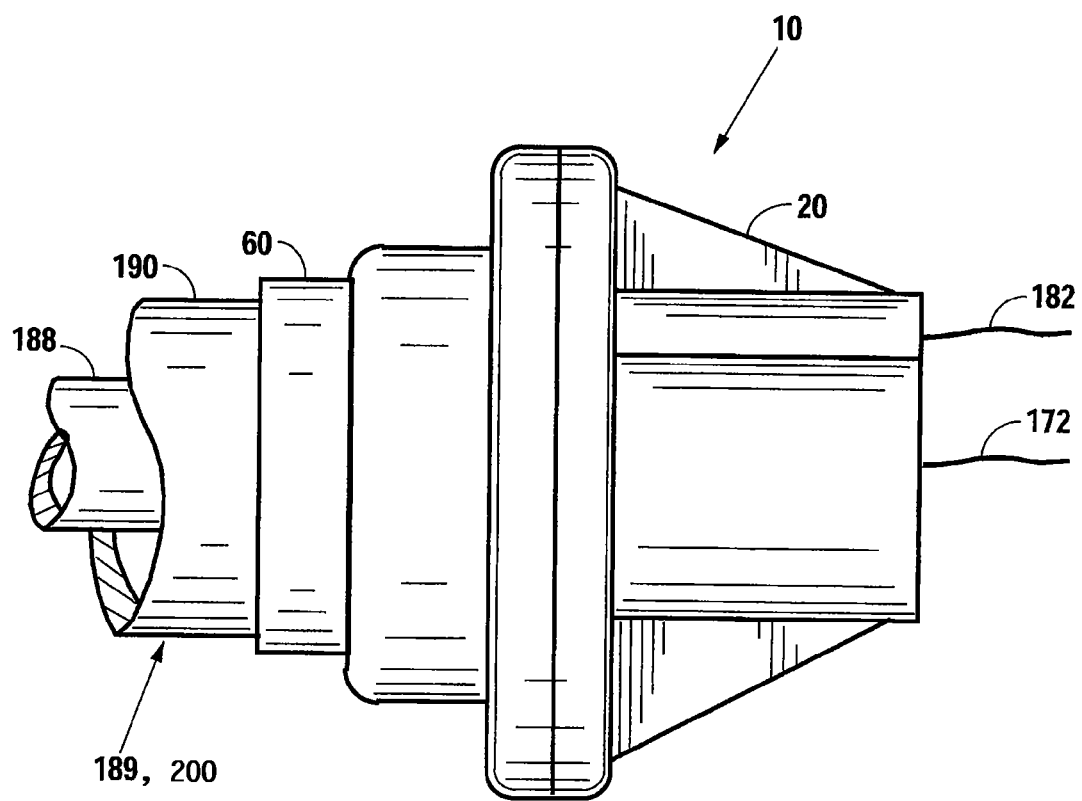
FIG. 1 is a side elevational view of the dual fluid connector of the present invention.
Figure 2:
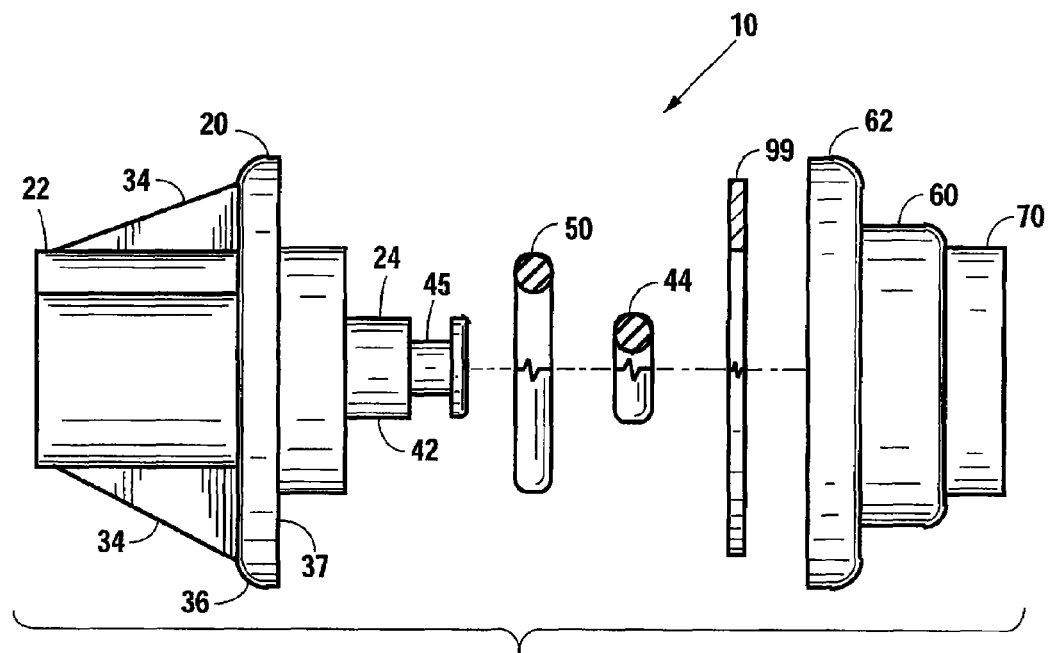
FIG. 2 is an exploded elevational view of the connector shown in FIG. 1.
Figure 3A:
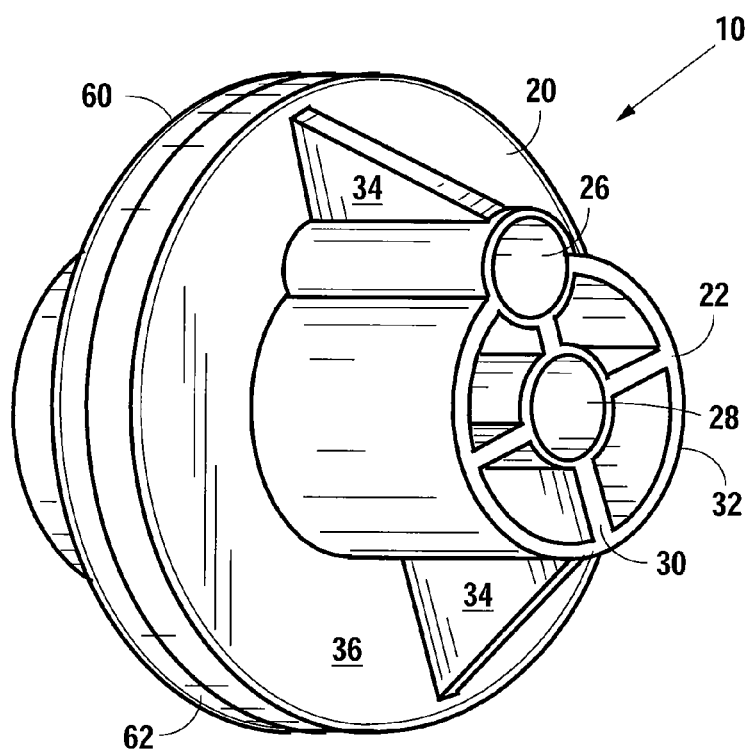
FIG. 3A is a perspective view from the rear of the connector shown in FIG. 1 showing the adjacent portals.

As may be seen in FIG. 2 and FIG. 3A, connector 10 has a rear body portion 20 with a rear side 22 and a front side 24. The rear side 22 of the rear body portion 20 has an opening or port 26 for fluidly coupling with tubing for delivering pressurized air to one end of a consumable (i.e. syringe) used in a fluid/gas exchange, and an opening or port 28 for fluidly coupling with tubing for delivering pressurized gas (i.e. $C_3F_8$ or $SF_6$) to an opposite end of such a consumable. Both openings 26, 28 are protected by a shroud 32. In the preferred embodiment, opening 28 for the gas tube is located substantially on the center line of the rear body portion 20, and opening 26 for the air tube is formed substantially adjacent to the opening 28. In the preferred embodiment, gussets 30 extend inwardly from the shroud 32 and support the opening 28 for the gas tube. The opening 26 for the air tube is formed as part of the shroud 32. The shroud 32 itself is supported by two gussets 34 extending from the flange portion 36 of the rear body portion 20.

Figure 4:
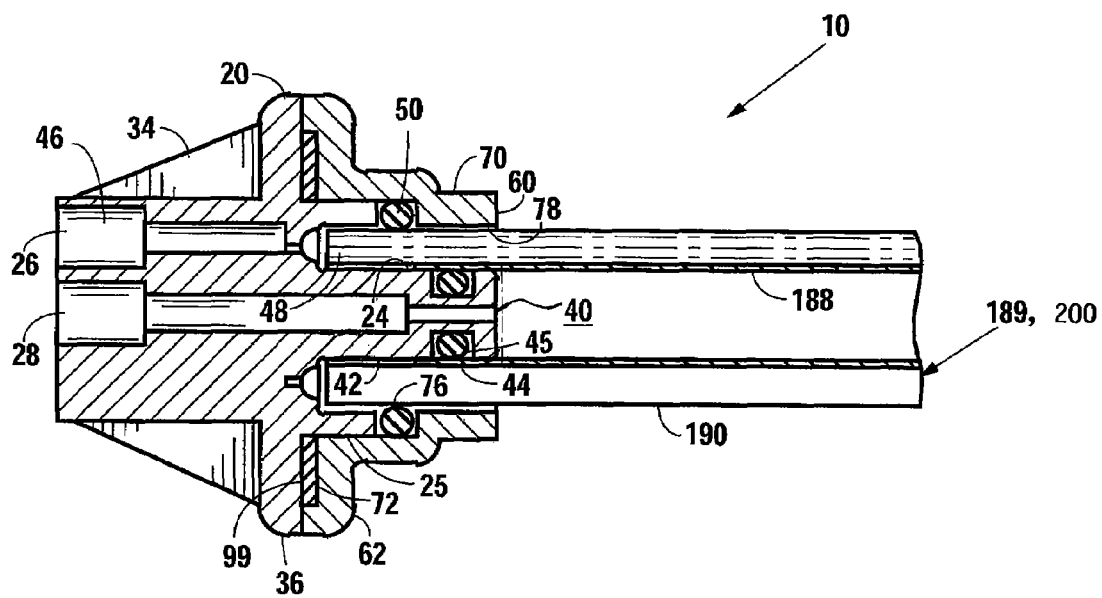
FIG. 4 is an elevational cross-sectional view of the connector shown in FIG. 1.

As may be seen in the sectional view of FIG. 4, on the front side 24 of the rear body portion 20 is an opening or port 40 for the pressurized gas. This opening 40 is located in a projection 42 extending from the front side 24 of the rear body portion 20. Surrounding the opening 40 is an o-ring 44 for fluidly sealing with a portion 188 of a manifold 189 of a vitrectomy console 200. Portion 188 is for delivering pressurized gas (i.e. $C_3F_8$ or $SF_6$). A ring-shaped flange 25 also extends from front side 24 of rear body portion 20. A passage 46 for the pressurized air ends in a substantially ring-shaped channel 48 defined by projection 42 and ring-shaped flange 25. An o-ring 50 is for fluidly sealing with a portion 190 of manifold 189. Portion 190 is for delivering pressurized air.

Figure 3B:
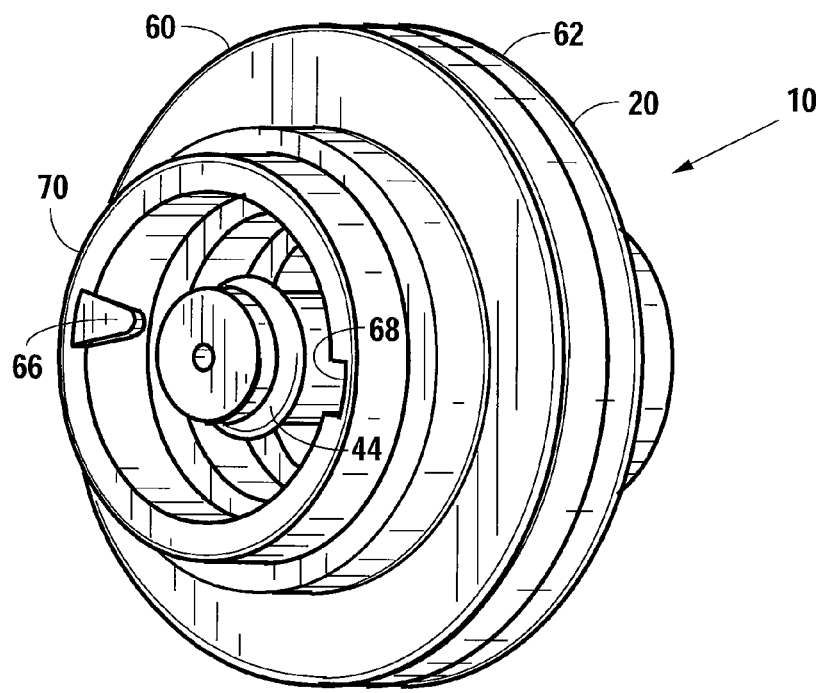
FIG. 3B is a perspective view from the front of the connector shown in FIG. 1 showing the concentric portals.

As shown in FIGS. 2, 3B, and 4, mating to the rear body portion 20 is a front body portion 60. The front body portion 60 includes a flange 62 which surrounds flange 25 of the rear body portion 20. Captured between the front body portion 20 and the rear body portion 60 is a substantially ring-shaped RFID (radio frequency identification) tag 99. A track engagement portion 66 and a slot 68 are formed as part of the front body portion 60 to facilitate connection to portion 190 of manifold 189. A shroud portion 70 protects the projection 42 and o-ring seals 45 and 50.

Referring back to FIG. 4, it may be seen that the RFID tag 99 fits within a recess 72 formed in the flange portion 62 of the front body portion 60. Those of ordinary skill in the art will understand that the recess 72 may also be formed in the flange portion 36 of the rear body portion 20.

In operation, front body portion 60 of connector 10 is fluidly coupled to manifold 189 of vitrectomy console 200, and rear body portion is fluidly coupled to a consumable (i.e. syringe) for use in a fluid/gas exchange. More specifically, pressurized gas (i.e. $C_3F_8$ or $SF_6$) from portion 188 of manifold 189 is delivered to opening 40. Pressurized air from portion 190 of manifold 189 is delivered to ring-shaped channel 48 and passageway 46. Pressurized gas is delivered to tubing 172 via opening 28. One end of tubing 172 is fluidly sealed within opening 28, and the other end of tubing 172 is fluidly coupled to a first end of a syringe used for performing the fluid/gas exchange. Pressurized air is delivered to tubing 182 via opening 26. One end of tubing 182 is fluidly sealed within opening 28, and the other end of tubing 182 is fluidly coupled to the second end of the syringe. Tubing 172 and 182 are preferably socket bonded within openings 28 and 26, respectively, using an adhesive.

Both the rear body portion 20 and the front body portion 60 of the disclosed connector 10 are made of a moldable plastic suitable for use with medical equipment. Once molded, a first smaller o-ring 44 is mounted within a recess 45 formed in projection 42. A second, larger o-ring 50 is inserted into a recess 76 formed by flange 25 and front body portion 60. The RDIF tag 99 is then inserted into the recess 76 when front body portion 60 and the rear body portion 20 are pushed together in an interfitting relationship.

The action of pushing the front body portion 20 and rear body portion 60 together does several things. First, contact of the RFID tag 99 with the flange 36 on the rear body portion 20 holds the RFID tag 99 in place. Second, when the outer surface of the projection 42 on the rear body portion 20 is slid into the larger opening 78 in the front body portion 60, a space 76 is formed which captures and positions the second or larger o-ring 50. Third, the flange 36 on the rear body portion 20 contacts the flange 62 on the front body portion 60. This contact allows for sonic welding of the flange 36 to the flange 62. While sonic welding of the rear body portion 20 to the front body portion 60 is used in the preferred embodiment, those of ordinary skill in the art will understand that other attachment methods may be used such as adhesive, spin-bonding or heat without departing from the scope of the disclosed invention.

While the dual fluid connector of the present invention has been disclosed according to its preferred and alternate embodiments, those of ordinary skill in the art will understand that yet other embodiments have been enabled by the foregoing disclosure. Such other embodiments shall be included within the scope and meaning of the appended claims.

What is claimed is:

1. A fluid connector, comprising:
   a rear body portion having:
      a rear side and a front side, the rear side having a center port and an off-center port, the front side having a center projection with a center opening and an annular groove for receiving an o-ring, a ring-shaped flange disposed around the center projection, and a ring-shaped channel defined by the center projection and the ring-shaped flange;
      a central passage extending through the rear body portion, the central passage originating at the center port and terminating at the center opening;
      an off-center passage extending through the rear body portion, the off-center passage originating at the off-center port and terminating at the ring-shaped channel;
   a front body portion constructed and arranged for interfitment over the ring-shaped flange of the rear body portion and for coupling with a manifold of a surgical console, whereby the front body portion shrouds the center projection and further defines the ring-shaped channel;
   the o-ring fluidly sealing with an interior surface of the manifold;
   the ring-shaped flange and the front body portion defining a second annular groove for receiving a second o-ring; and
   the second o-ring fluidly sealing with an exterior surface of the manifold.

2. The fluid connector of claim 1 wherein the manifold is for providing pressurized gas to the center opening and pressurized air to the ring-shaped channel.

3. The fluid connector of claim 2 wherein the pressurized gas is a retinal tamponading gas.

4. The fluid connector of claim 1 further comprising a radio frequency identification tag disposed within the connector.

5. The fluid connector of claim 1 further comprising:
   a first tubing having a first end fluidly sealed within the center port; and
   a second tubing having a first end fluidly sealed within the off-center port.

6. The fluid connector of claim 5 wherein:
   the first end of the first tubing is socket bonded within the center port; and
   the first end of the second tubing is socket bonded within the off-center port.

7. The fluid connector of claim 6 wherein the socket bonding is accomplished via an adhesive.

8. A fluid connector system, comprising:
   a fluid connector having:
      a rear body portion having:
         a rear side and a front side, the rear side having a center port and an off-center port, the front side having a center projection with a center opening, a ring-shaped flange disposed around the center projection, and a ring-shaped channel defined by the center projection and the ring-shaped flange;
         a central passage extending through the rear body portion, the central passage originating at the center port and terminating at the center opening;
         an off-center passage extending through the rear body portion, the off-center passage originating at the off-center port and terminating at the ring-shaped channel; and
      a front body portion constructed and arranged for interfitment over the ring-shaped flange of the rear body portion, whereby the front body portion shrouds the center projection and further defines the ring-shaped channel; and
   a manifold disposed within a surgical console having:
      a first portion fluidly sealed to the center projection for providing pressurized gas to the fluid connector; and
      a second portion fluidly sealed to the rear body portion and the front body portion for providing pressurized air to the ring-shaped channel.

9. The fluid connector system of claim 8 wherein:

the center projection has an annular groove for receiving an o-ring, and the o-ring fluidly seals with an interior surface of the first portion of the manifold.

10. The fluid connector system of claim 9 wherein:

the ring-shaped flange and the front body portion define a second annular groove for receiving a second o-ring, and the second o-ring fluidly seals with an exterior surface of the second portion of the manifold.

11. The fluid connector system of claim 8 wherein the pressurized gas is a retinal tamponading gas.

12. The fluid connector system of claim 8 further comprising a radio frequency identification tag disposed within the connector.

* * * * *